US012205722B2

(12) United States Patent
Ferrante et al.

(10) Patent No.: US 12,205,722 B2
(45) Date of Patent: Jan. 21, 2025

(54) SYSTEMS FOR DETECTING AND IDENTIFYING COINCIDENT CONDITIONS

(71) Applicant: Digital Diagnostics Inc., Coralville, IA (US)

(72) Inventors: Joseph Ferrante, Cambridge, MA (US); Elliot Swart, Phoenix, AZ (US)

(73) Assignee: Digital Diagnostics Inc., Coralville, IA (US)

( * ) Notice: Subject to any disclaimer, the term of this patent is extended or adjusted under 35 U.S.C. 154(b) by 342 days.

(21) Appl. No.: 17/623,533

(22) PCT Filed: Jun. 30, 2020

(86) PCT No.: PCT/US2020/040270
§ 371 (c)(1),
(2) Date: Dec. 28, 2021

(87) PCT Pub. No.: WO2021/003142
PCT Pub. Date: Jan. 7, 2021

(65) Prior Publication Data
US 2022/0367049 A1    Nov. 17, 2022

Related U.S. Application Data

(60) Provisional application No. 62/869,553, filed on Jul. 1, 2019.

(51) Int. Cl.
*G16H 30/20* (2018.01)
*G16H 50/20* (2018.01)

(52) U.S. Cl.
CPC ............. *G16H 50/20* (2018.01); *G16H 30/20* (2018.01)

(58) Field of Classification Search
CPC ....................................................... G16H 50/20
See application file for complete search history.

(56) References Cited

U.S. PATENT DOCUMENTS 10,140,421 B1 * 11/2018 Bernard ................. G01T 1/247
2012/0008838 A1    1/2012 Guyon et al.
(Continued)

FOREIGN PATENT DOCUMENTS

CN    103324940 A    9/2013
CN    107480769 A    12/2017
(Continued)

OTHER PUBLICATIONS

A. Albahar. "Skin Lesion Classification using Convolutional Neural Network with Novel regularizer" IEEE, Mar. 2019 (Year: 2019).*
(Continued)

*Primary Examiner* — Oneal R Mistry
(74) *Attorney, Agent, or Firm* — Fenwick & West LLP

(57) ABSTRACT

A diagnosis system trains a set of machine-learned diagnosis models that are configured to receive an image of a patient and generate predictions on whether the patient has one or more health conditions. In one embodiment, the set of machine-learned models are trained to generate predictions for images that contain two or more underlying health conditions of the patient. In one instance, the symptoms for the two or more health conditions are shown as two or more overlapping skin abnormalities on the patient. By using the architectures of the set of diagnosis models described herein, the diagnosis system can generate more accurate predictions for images that contain overlapping symptoms for two or more health conditions compared to existing systems.

24 Claims, 12 Drawing Sheets

(56) References Cited

U.S. PATENT DOCUMENTS

| | | | |
|---|---|---|---|
| 2014/0088440 | A1 | 3/2014 | Swart et al. |
| 2015/0206022 | A1 | 7/2015 | Radha et al. |
| 2015/0230712 | A1 | 8/2015 | Aarabi |
| 2018/0122076 | A1 | 5/2018 | Abedini et al. |
| 2018/0146912 | A1 | 5/2018 | Rundo et al. |
| 2019/0198156 | A1 | 6/2019 | Madani et al. |
| 2020/0327470 | A1* | 10/2020 | Trim .................. G06Q 10/0635 |
| 2022/0254019 | A1* | 8/2022 | Connor .................. G16H 40/67 |

FOREIGN PATENT DOCUMENTS

| | | |
|---|---|---|
| CN | 107945173 A | 4/2018 |
| CN | 108198620 A | 6/2018 |
| DE | 102017010397 A1 | 5/2019 |
| JP | 2005-192944 A | 7/2005 |
| JP | 2016-198197 A | 12/2016 |
| JP | 2017-045341 A | 3/2017 |

OTHER PUBLICATIONS

Albahar. "Skin Lesion Classification using Convolutional Neural Network with Novel regularizer" IEEE, Mar. 2019 (Year: 2019).*

Canadian Intellectual Property Office, Office Action, Canadian Patent Application No. 3,141,644, Mar. 31, 2023, 3 pages.

European Patent Office, Extended European Search Report and Written Opinion, European Patent Application No. 20834431.7, May 19, 2023, 13 pages.

Giacinto, G. et al. "Design of Effective Neural Network Ensembles for Image Classification Purposes," *Image and Vision Computing*, vol. 19, No. 9-10, Aug. 1, 2001, pp. 1-23.

Harangi, B. "Skin Lesion Classification with Ensembles of Deep Convolutional Neural Networks," *Journal of Biomedical Informatics*, vol. 86, Oct. 1, 2018, pp. 25-32.

Korotkov, K. et al. "Computerized Analysis of Pigmented Skin Lesions: A Review," *Artificial Intelligence in Medicine*, vol. 56, No. 2, Oct. 1, 2012, pp. 69-90.

Zhang, X. et al. "Towards Improving Diagnosis of Skin Diseases by Combining Deep Neural Network and Human Knowledge," *BMC Medical Informatics and Decision Making*, vol. 18, No. 2, Jul. 23, 2018, pp. 69-76.

AIM. "Is Age a Risk Factor for Melanoma?" AIM at Melanoma Foundation, 2022, 5 pages, [Online] [Retrieved Oct. 21, 2022], Retrieved from the Internet <URL:https://www.aimatmelanoma.org/melanoma-101/understanding-melanoma/melanoma-risk-factors/age-and-risk/>.

Zhou, Z-Q. et al. "Object Detection with Deep Learning: A Review." IEEE Transactions on Neural Networks and Learning Systems, vol. 30, No. 11, Nov. 2019, pp. 3212-3232.

PCT International Search Report and Written Opinion, International Application No. PCT/US2020/040270, dated Oct. 14, 2020, 7 Pages.

Marvdashti et al. "Classification of basal cell carcinoma in human skin using machine learning and quantitative features captured by polarization sensitive optical coherence tomography", vol. 7, No. 9 | Sep. 1, 2016 | Biomedical Optics Express 3722. Retrieved on Apr. 9, 2020. Retrieved from <URL: https://www.osapublishing.org/DirectPDFAccess/13975890-93D4-4AB7-89B6C833A020714B_349605/boe-7-9-3721.pdf?da=1&id=349605&seq=0&mobile=no> entire document.

Patnaik et al., "Automated Skin Disease Identification using Deep Learning Algorithm", Biomedical & Pharmacology Journal, vol. 11(3), p. 1429-1436, Sep. 2018. Retrieved on Sep. 4, 2020. Retrieved from <URL: https://search.proquest.com/docview/2264144219/fulltextPDF/73DB91E1E7044458PQ/1?Accountid=1429944> entire document.

Japan Patent Office, Office Action with English Translation, Japanese Patent Application No. 2021-576048, Jun. 4, 2024, 12 pages.

China National Intellectual Property Administration, Office Action with English Translation, Chinese Patent Application No. 202080048294.9, May 7, 2024, 11 pages.

\* cited by examiner

SYSTEMS FOR DETECTING AND IDENTIFYING COINCIDENT CONDITIONS

CROSS-REFERENCE TO RELATED APPLICATIONS

This application is a National Stage Entry of PCT/US2020/040270 which claims the benefit of and priority to U.S. Provisional Application No. 62/869,553, filed Jul. 1, 2019, which is hereby incorporated by reference in its entirety.

BACKGROUND

This disclosure relates generally to diagnosis of health abnormalities, and more particularly to diagnosis of overlapping health conditions in an image.

Computerized diagnostic systems are configured to receive images of a patient and generate predictions on whether the patient has one or more health conditions based on the presence of symptoms in the image. Computerized diagnostic systems can be applied to predict health conditions in various anatomical parts of the patient. For example, a skin diagnostic system can be applied to predict whether an image of a patient's skin has one or more skin abnormalities, such as a rash, a mole, eczema, acne, and cold sores. As another example, a tumor diagnostic system can be applied to predict whether an image of a patient's anatomy contains a tumor.

Often times, a patient can have multiple health conditions that appear in the same image. For example, an image may contain a psoriatic plaque and a nevus, both skin abnormalities, located on the same arm that are spatially separated from each other. As another example, an image may contain skin abnormalities that overlap with each other, such as a psoriatic plaque having a mole within its borders. However, existing computerized diagnostic systems have difficulty generating accurate diagnoses in these instances because, for example, the computerized diagnostic system has been trained to generate predictions for a single health condition. Moreover, when health conditions overlap, presentation and other symptoms in the image can be the result of either condition individually or both in combination and may be difficult for the computerized diagnostic system to accurately differentiate symptoms in the image to the respective health condition.

SUMMARY

A diagnosis system trains a set of machine-learned diagnosis models that are configured to receive an image of a patient and generate predictions on whether the patient has one or more health conditions. In one embodiment, the set of machine-learned models are trained to generate predictions for images that include two or more underlying health conditions of the patient. In one instance, the symptoms for the two or more health conditions are shown as two or more overlapping skin abnormalities on the patient. By using the architectures of the set of diagnosis models described herein, the diagnosis system can generate more accurate predictions for images that include overlapping symptoms for two or more health conditions compared to existing systems.

In an embodiment, the diagnosis system receives, from a client device, a request to diagnose skin abnormalities in an input image. The input image includes overlapping symptoms for two or more skin abnormalities on the skin. The diagnosis system accesses a set of machine-learned diagnosis models from a database. Each machine-learned model includes a respective set of trained weights that were determined through a training process. The diagnosis system generates a respective prediction for each of two or more skin abnormalities in the input image by applying the set of diagnosis models to the input image. A prediction indicates a likelihood that a respective skin abnormality in the two or more skin abnormalities are shown in the input image. The diagnosis system generates a diagnosis of the skin abnormalities from the predictions for the input image and provides the diagnosis to the client device.

In one embodiment, a diagnosis system trains a set of machine-learned indicator models that are configured to receive an image of a patient or individual and generate an indication on whether the input image presents two or more health conditions. In one embodiment, the diagnosis system receives a request for diagnoses of health conditions in an input image. The diagnosis system accesses an indicator model or a diagnosis model with indicator functionality from a database. The diagnosis system generates an indication representing a likelihood that the input image includes two or more health conditions by applying the indicator model to the input image. The diagnosis system makes a determination on whether the input image presents two or more health conditions from the indication generated for the input image. The diagnosis system generates a result for the request based on the determination, and provides the result to the user of the client device.

Since input images presenting multiple health conditions may be difficult to diagnose, the user of the client device can receive such an indication, in addition to or alternatively to an active diagnoses of the image. The user can then determine to provide the input image to a medical expert to obtain a more accurate diagnoses. Thus, it may be advantageous for the user of the computerized diagnostic system to receive information on whether the input image includes symptoms from two or more health conditions such that a more accurate diagnoses can be made by a different expert system or a medical expert.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
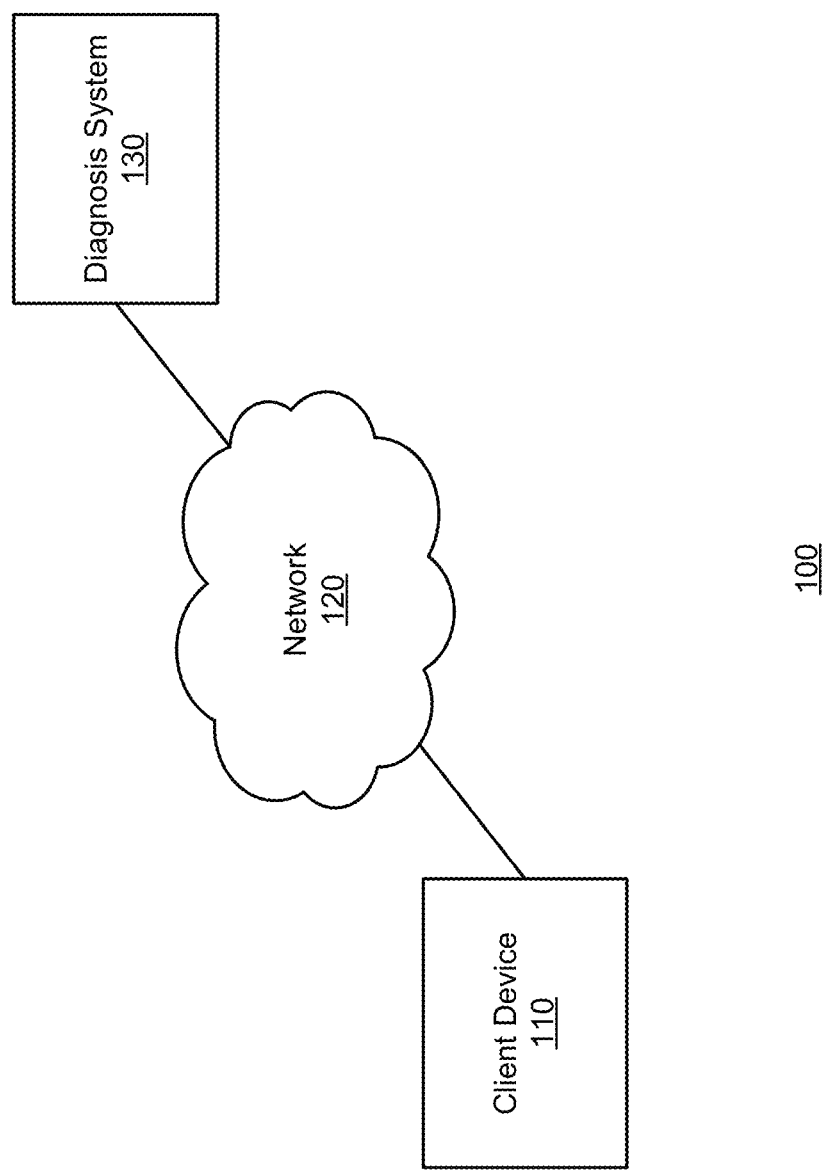
FIG. 1 is a high level block diagram of a system environment for a diagnosis system, in accordance with an embodiment.

FIG. 1 is a high level block diagram of a system environment for a diagnosis system, in accordance with an embodiment. The system environment 100 shown by FIG. 1 includes one or more client devices 110, a network 120, and a diagnosis system 130. In alternative configurations, different and/or additional components may be included in the system environment 100.

The diagnosis system 130 is a system for providing various types of computerized diagnosis to users of client devices 110. The diagnosis system 130 may receive images of a patient's anatomical part and generate predictions on whether the patient has one or more health conditions based on the image. For example, the diagnosis system 130 may receive an image of a patient's skin and generate predictions on whether the patient has one or more skin abnormalities, such as a rash, a mole, eczema, acne, and cold sores. As another example, the diagnosis system 130 may receive a radiology image of a patient's brain and generate predictions on whether the patient has a brain tumor. The predictions generated by the diagnosis system 130 can be used as stand-alone diagnoses or can be used to assist, for example, medical doctors at a hospital in the interpretation of the images of the patient.

The diagnosis system 130 trains a set of machine-learned diagnosis models that are configured to receive an image of a patient and generate predictions on one or more health conditions. The images received by the diagnosis system 130 may be medical images obtained at a hospital, such as radiology images, computerized tomography (CT) scans, medical resonance imaging (MRI) scans, X-ray images, ultrasound or ultrasonography images, tactile images, or thermography images. In another instance, the images may be pictures taken by individual users of the client device 110 (e.g., at home or in the office). The images may show symptoms or other presentations on an anatomical part of the patient, which the diagnosis system 130 can use to infer health conditions that are responsible for generating these symptoms.

In one embodiment, the diagnosis system 130 trains the set of machine-learned models to generate predictions for images that include symptoms for two or more health conditions of the patient. Specifically, a patient can have symptoms from multiple health conditions that appear in the same image. For example, an image may contain a psoriatic plaque and a nevus, both skin abnormalities, located on the same arm that are spatially separated from each other. As another example, an image may include skin abnormalities that overlap with each other, such as a psoriatic plaque having a mole within its borders. However, existing computerized diagnostic systems may have difficulty generating accurate diagnoses in these instances, especially when the symptoms overlap since the symptoms may be the result of the individual or an unknown combination of the underlying health conditions of the patient. Moreover, existing diagnosis systems may be configured to generate predictions for a single condition. Thus, even if an existing diagnosis system is able to detect one of the health conditions in an image, the detected condition would be at the exclusion of the remaining health conditions in the image, leading to missed diagnoses that could lead to significant health problems for the subject of the image.

During the inference process, the diagnosis system 130 receives a request to diagnose health conditions in an input image. The input image includes overlapping symptoms from two or more health conditions of the patient. The diagnosis system 130 accesses a set of machine-learned diagnosis models from a database. Each machine-learned model includes a respective set of trained weights that were determined through a training process. The diagnosis system 130 generates a respective prediction for each of the two or more health conditions in the input image by applying a set of diagnosis models to the input image. A prediction indicates a likelihood that the input image shows symptoms from a respective health condition. The diagnosis system 130 generates a diagnosis of the input image from the predictions and provides the diagnosis back to the client device 110.

In one particular embodiment referred throughout the remainder of the specification, the two or more health conditions are two or more skin abnormalities that have overlapping symptoms presented on the skin of the patient. For example, a mole may appear in an area of the skin with a rash. As another example, an area of the skin with eczema may overlap with a part of the skin with contact dermatitis. However, it is appreciated that in other embodiments, the two or more health conditions can be any type of health-related conditions, such as diseases or allergies that can produce overlapping or spatially separated symptoms in the same anatomical part of a patient. For example, the two or more health conditions may be different types of tumors, blood diseases, and the like, that individually or in combination can present symptoms on a patient.

Figure 2:
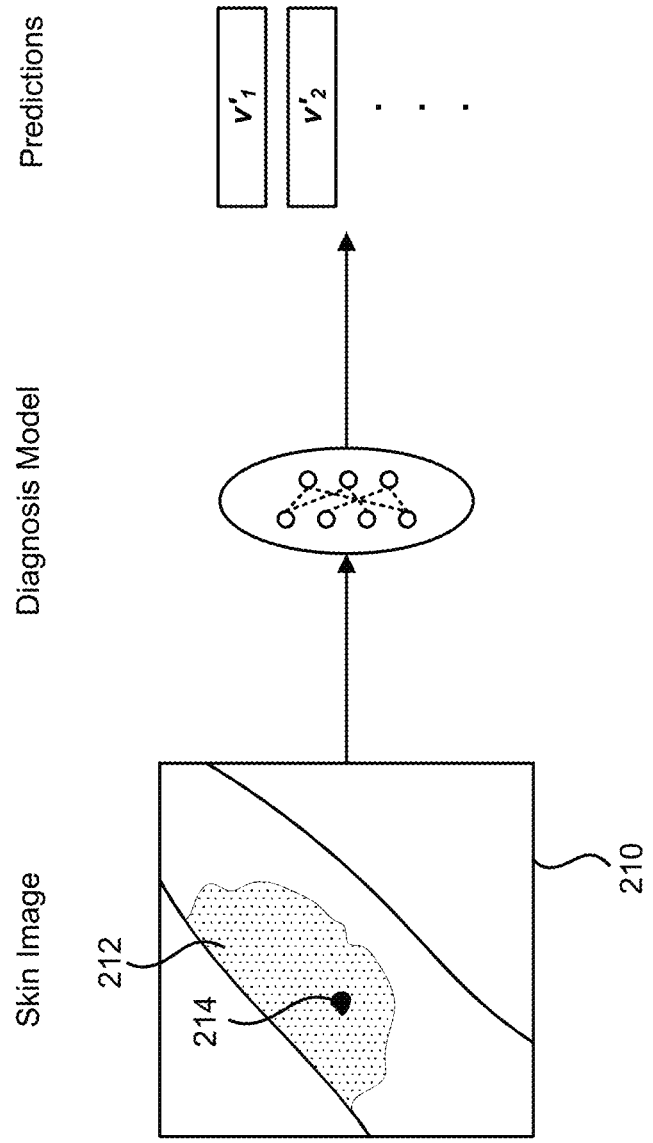
FIG. 2 illustrates a general inference process for a diagnosis model, in accordance with an embodiment.

FIG. 2 illustrates a general inference process for a diagnosis model, in accordance with an embodiment. The diagnostic system 130 receives an input image 210 of a patient suspected to have skin abnormalities. Specifically, the input image 210 shows a first skin abnormality 212 and a second skin abnormality 214 overlapping with each other on an arm of a patient. The diagnostic system 130 accesses a set of machine-learned diagnostic models from a database. The diagnosis system 130 applies the diagnosis models to the input image 210 to generate two or more predictions $v'_1, v'_2, \ldots, v'_n$ for the input image 210. A prediction $v'_i$ may indicate a likelihood that the input image 210 includes symptoms from a respective skin abnormality i. In the example shown in FIG. 2, the prediction $v'_1$ may indicate a high likelihood that the input image 210 includes a mole and the prediction $v'_2$ may indicate a high likelihood that the input image 210 also includes a rash. The remaining predictions for other skin abnormalities may be associated with a significantly low likelihood. The diagnosis system 130 determines a diagnosis that the input image 210 includes a mole and a skin rash by selecting the subset of predictions with likelihoods above a predetermined threshold and provides the client device 110 with the diagnoses.

Returning to the system environment of FIG. 1, the diagnosis system 130 generally trains the respective set of weights for the diagnosis models using a training corpus of images and labels to reduce a loss function. The loss function for a diagnosis model indicates a difference between estimated outputs generated by applying the diagnosis model with an estimated set of weights to input data in the training corpus that the diagnosis model is configured to receive, and actual labels in the training corpus that represent the types of data the diagnosis model is configured to predict. The estimated set of weights for the diagnosis model is repeatedly updated to reduce the loss function until a predetermined criteria is reached. The training process for the set of diagnosis models are described in more detail in conjunction with FIG. 9.

As described herein, FIGS. 3 through 7 illustrate various architectures of the set of diagnosis models that can be used by the diagnosis system 130 to generate predictions for two or more health conditions presented in an image during the inference process. Each architecture described below may include a set of trained weights that were determined through the training process, which will be described in conjunction with FIG. 9. By using the architectures of the set of diagnosis models described herein, the diagnosis system can generate more accurate predictions for images that include two or more overlapping health conditions compared to existing systems.

Figure 3:
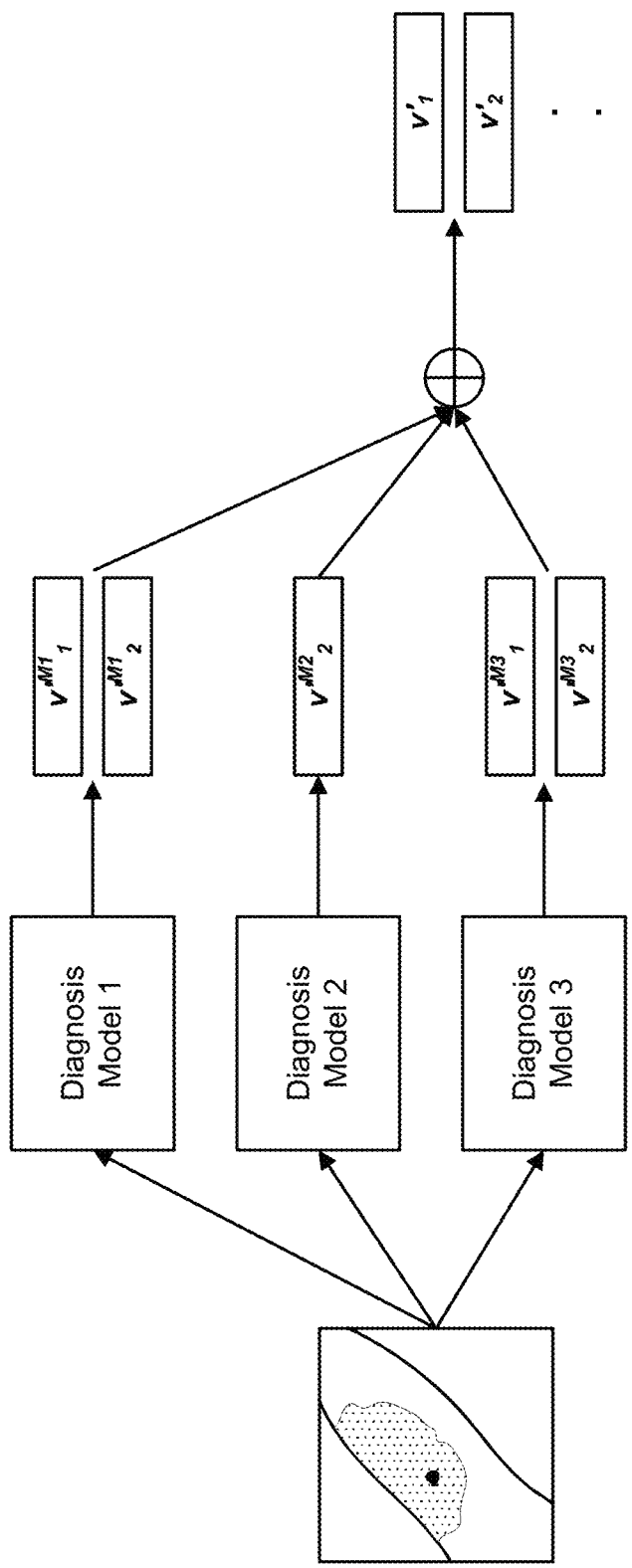
FIG. 3 illustrates an example inference process for a set of machine-learned diagnosis models with an ensemble architecture, in accordance with an embodiment.

FIG. 3 illustrates an example inference process for a set of machine-learned diagnosis models with an ensemble architecture, in accordance with an embodiment. In one embodiment, the set of diagnosis models includes an ensemble set of machine-learned diagnosis models. Specifically, each diagnosis model in the ensemble is configured to receive an input image and generate one or more predictions on whether the patient has one or more health conditions by applying a set of trained weights for the diagnosis model. In the example shown in FIG. 3, the ensemble set of diagnosis models includes "Diagnosis Model 1," "Diagnosis Model 2," and "Diagnosis Model 3."

A diagnosis model in the ensemble set is configured to generate predictions for a different or same set of health conditions from other diagnosis models in the ensemble set. In the example shown in FIG. 3, "Diagnosis Model 1" may be configured to generate a prediction $v'^{M1}_1$ indicating a likelihood that the input image includes a mole and a prediction $v'^{M1}_2$ indicating a likelihood that the input image includes a rash. As another example, "Diagnosis Model 2" may be configured to generate a single prediction $v'^{M2}_1$ indicating a likelihood that the input image includes a rash, and "Diagnosis Model 3" may be configured to generate a prediction $v'^{M3}_1$ indicating a likelihood that the input image includes a mole and a prediction $v'^{M3}_2$ indicating a likelihood that the input image includes acne.

During the inference process, the diagnosis system 130 generates the respective prediction for each of the two or more health conditions in the input image by applying the ensemble set of diagnosis models to the input image and combining the predictions from the ensemble set for each respective health condition. In one instance, the prediction for a respective health condition is generated by computing an average of the predictions for the health conditions that were generated by the ensemble set. In the example shown in FIG. 3, the prediction $v'_1$ indicating a likelihood that the patient has a rash is generated by averaging the predictions $v'^{M1}_2$, $v'^{M2}_1$ from "Diagnosis Model 1" and "Diagnosis Model 2." However, it is appreciated that in other embodiments, the predictions from the diagnosis models in the ensemble can be combined in any other way than an average. The diagnosis system 130 determines diagnoses by selecting the subset of predictions with likelihoods above a predetermined threshold.

In one embodiment, a diagnosis model in the ensemble set can be configured to generate multiple outputs that do not necessarily correspond to the same sequence of health conditions every time the diagnosis model is applied to an input image. In such an embodiment, the diagnosis system 130 may group predictions from the ensemble set by similarity of the predictions and intermediate features, and the predictions for the two or more health conditions presented in the input image may be generated by combining the predictions from each identified group. In another instance, the diagnosis system 130 may group predictions from the ensemble set by similar locations using, for example, an attention model, and the predictions for the two or more health conditions in the input image may be generated by combining the predictions for each identified location.

Figure 4:
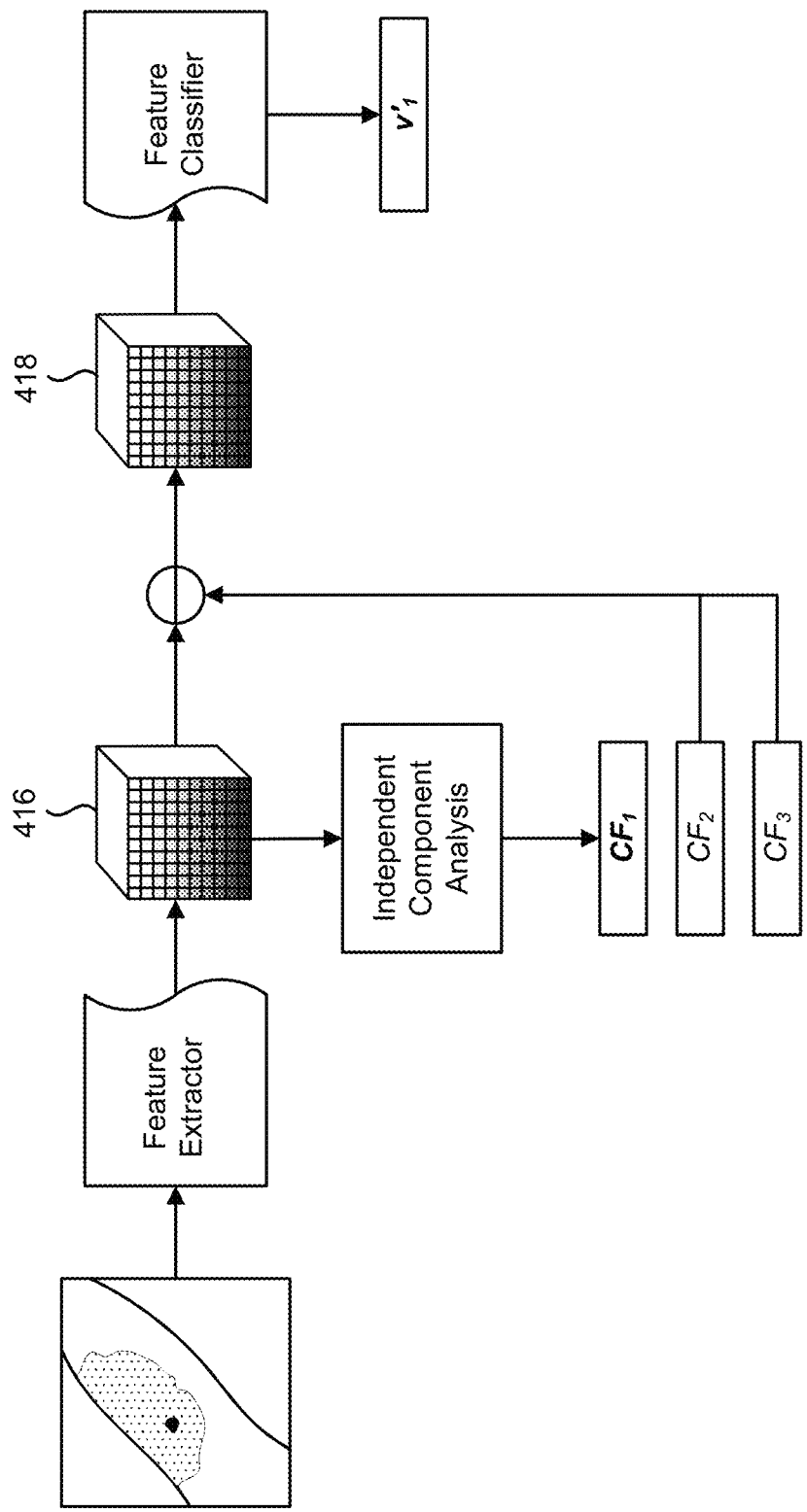
FIG. 4 illustrates an example inference process using independent component analysis (ICA) in conjunction with a set of diagnosis models, in accordance with an embodiment.

FIG. 4 illustrates an example inference process using independent component analysis (ICA) in conjunction with a set of diagnosis models, in accordance with an embodiment. In one embodiment, the set of diagnosis models includes a feature extractor model, an independent component analysis (ICA) model, and a feature classifier model. The feature extractor model is configured to receive an input image and generate an image tensor characterizing a plurality of spatial features in the input image by applying a first set of trained weights. The ICA model is configured to receive the image tensor and extract a plurality of components from the image tensor. The feature classifier model is configured to receive a component and generate a prediction that indicates a likelihood of a respective health condition for the component by applying a second set of trained weights.

During the inference process, the diagnosis system 130 generates an image tensor 416 for the input image by applying the feature extractor model to the input image. The diagnosis system 130 performs ICA to extract the plurality of components $CF_1$, $CF_2$, $CF_3$, . . . , $CF_n$ from the image tensor 416, considering each spatial location in the image tensor 416 as an observation. For each extracted component, the diagnosis system 130 computes the contribution of the component to the image tensor 416 to generate a respective tensor for the component. In one instance, the respective tensor for the component is generated by computing the contributions of the remaining components in the plurality of components and subtracting the contributions of the remaining components from the image tensor 416. In the example shown in FIG. 4, the respective tensor 418 for component $CF_1$ is generated by computing the contributions of the remaining components $CF_2$, $CF_3$, . . . , $CF_n$ and subtracting the contributions from the image tensor 416. While FIG. 4 illustrates only the respective tensor 418 for component $CF_1$, this process may be repeated to generate respective tensors for each of the remaining components $CF_2$, $CF_3$, . . . , $CF_n$.

For each tensor, the diagnosis system 130 generates a prediction by applying the feature classifier model to the tensor for the component. In the example shown in FIG. 4, the prediction $v'_1$ for the component $CF_1$ is generated by applying the feature classifier model to the tensor 418 for the component. While FIG. 4 illustrates only the prediction $v'_1$ for component $CF_1$, this process may be repeated to generate respective predictions from each of the remaining components $CF_2, CF_3, \ldots, CF_n$ by applying the feature classifier model to the tensor for each component. The diagnosis system 130 determines diagnoses based on the predictions $v'_1, v'_2, \ldots, v'_n$ by selecting a subset with likelihoods above a threshold.

Based on the number of components extracted from the image tensor, the diagnoses may each correspond to different health conditions underlying the input image, or a subset of the diagnoses may correspond to the same health condition if the number of extracted components is greater than the number of health conditions included in the input image. In one instance, the diagnosis system 130 extracts a predetermined number of components based on an estimated number of health conditions in the input image. In another instance, the diagnosis system 130 performs ICA with an increasing number of components, and iteratively generates predictions and diagnoses with each new component. The diagnosis system 130 completes the inference process when further increasing the number of components does not increase the number of unique diagnoses, and there is convergence in a criterion function for the ICA. In one instance, there may be a threshold number of added components for determining convergence. For example, three components may be added while the set of diagnoses is unchanged to be considered for convergence.

In another embodiment, the plurality of components is extracted beforehand during the training process. During the inference process, the diagnosis system 130 decomposes the image tensor into a mixture of the plurality of components and computes the contribution of each predetermined component to the image tensor to generate a respective tensor for each component. The diagnosis system 130 identifies a subset of components that have a contribution above a threshold. For each tensor, the diagnosis system 130 generates a prediction by applying the feature classifier model to the tensor for the component in the subset. In some embodiments, each predetermined component may be pre-classified and stored using the feature classifier model. The classification results are then determined by using the stored components associated with the contributing components.

Figure 5:
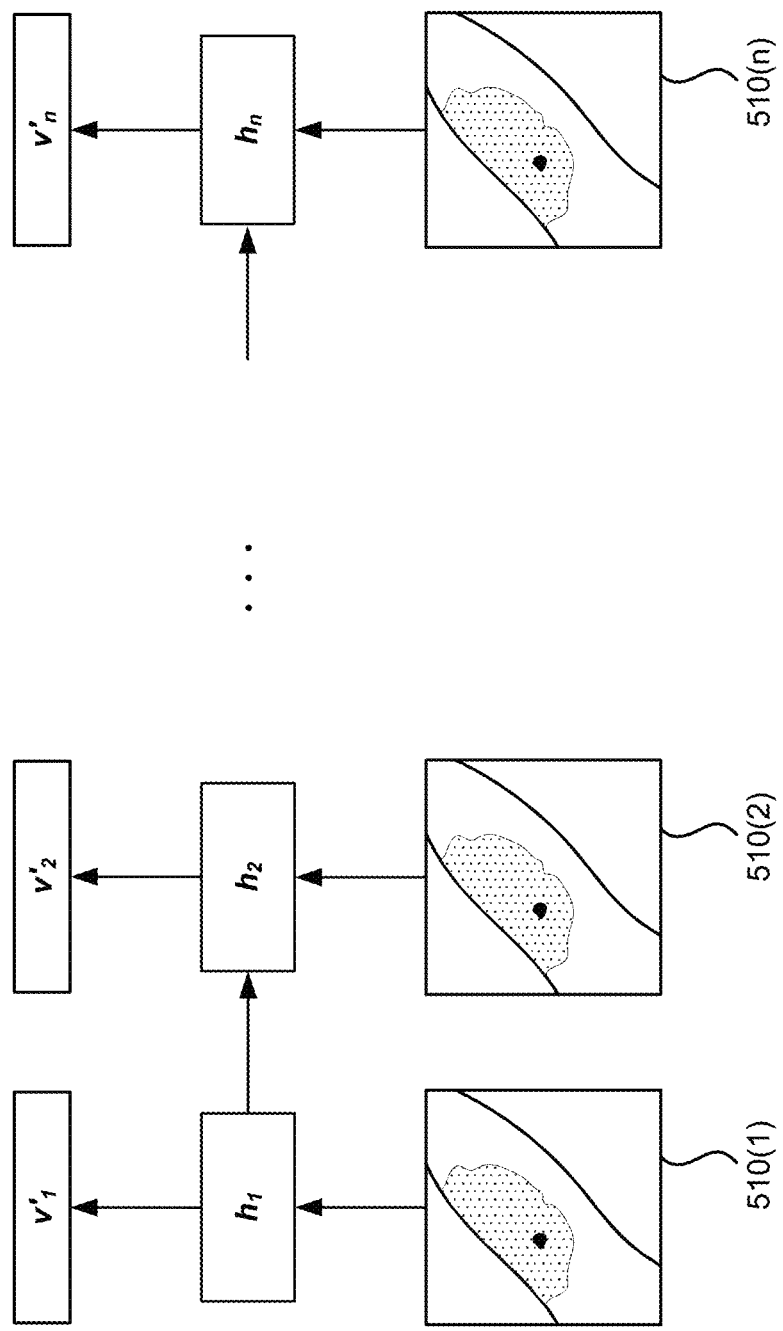
FIG. 5 illustrates an example inference process for a diagnosis model with a recurrent neural network (RNN) architecture, in accordance with an embodiment.

FIG. 5 illustrates an example inference process for a diagnosis model with a recurrent neural network (RNN) architecture, in accordance with an embodiment. In one embodiment, the set of diagnosis model includes a diagnosis model with an RNN architecture that includes one or more neural network layers with a set of weights. The RNN architecture is configured to receive a sequence of images and sequentially generate predictions for two or more health conditions presented in the sequence of images. The sequence of input images may be a repeated sequence of the same input image or may be a sequence of images that capture the anatomical part of the patient at issue at different views, perspectives, filters, and the like. In the example shown in FIG. 5, the sequence of images 510(1), 510(2), . . . , 510(n) are identical images of the skin of an arm of a patient. However, in another example, the sequence of images may include images of the same arm captured from different viewpoints or in different color scales.

Specifically, for a current image in the sequence, the RNN architecture is configured to receive the current image 510(i) and a hidden state $h_{i-1}$ for a previous iteration and generate a hidden state $h_i$ for the current image 510(i) by applying a first set of trained weights. The RNN architecture is further configured to receive the hidden state for the current image $h_i$ and generate a prediction $v_i$ for a respective health condition by applying a second set of trained weights. After each iteration, the RNN architecture may be further configured to determine whether the diagnosis model should generate predictions for other health conditions in the input image or should complete the inference process. If the RNN architecture determines to continue generating predictions, the RNN architecture receives the next image 510(i+1) in the sequence and generates a prediction $v_{i+1}$ for another health condition. This process is repeated until the RNN architecture determines to complete the inference process. In the example shown in FIG. 5, the prediction $v'_1$ may indicate that the input image includes a mole, while the next prediction $v'_2$ may indicate that the input image includes a rash.

In one embodiment, the RNN architecture is further configured to receive a memory vector $m_i$ at each iteration in addition to the current image 510(i) and the hidden state $h_{i-1}$ for a previous iteration, and generate the prediction $v_i$ for a respective health condition from the current image 510(i). The memory vector $m_i$ may represent a vector that includes information on which health conditions have already been classified up to the current iteration i. For example, the memory vector $m_i$ may be an aggregate of previous predictions or previous diagnoses up to the current iteration. In the example shown in FIG. 5, the memory vector $m_2$ at the second iteration may indicate that a prediction or diagnosis for a mole had been made up to the second iteration based on $v_1$. By further configuring the RNN architecture to receive memory vectors, the diagnosis system 130 may structure the diagnosis model to generate predictions for health conditions that have not been previously predicted at each iteration of the inference process.

During the inference process, the diagnosis system 130 generates the respective prediction for each of the two or more health conditions by repeatedly applying the RNN architecture to the sequence of input images. In one embodiment, when the RNN architecture is further configured to receive memory vectors, the diagnosis system 130 may obtain a respective memory vector for an iteration based on the predictions that have been generated up to the current iteration. The diagnosis system 130 generates the respective prediction for each of the two or more health conditions by repeatedly applying the RNN architecture to the sequence of images and the memory vectors.

Figure 6:
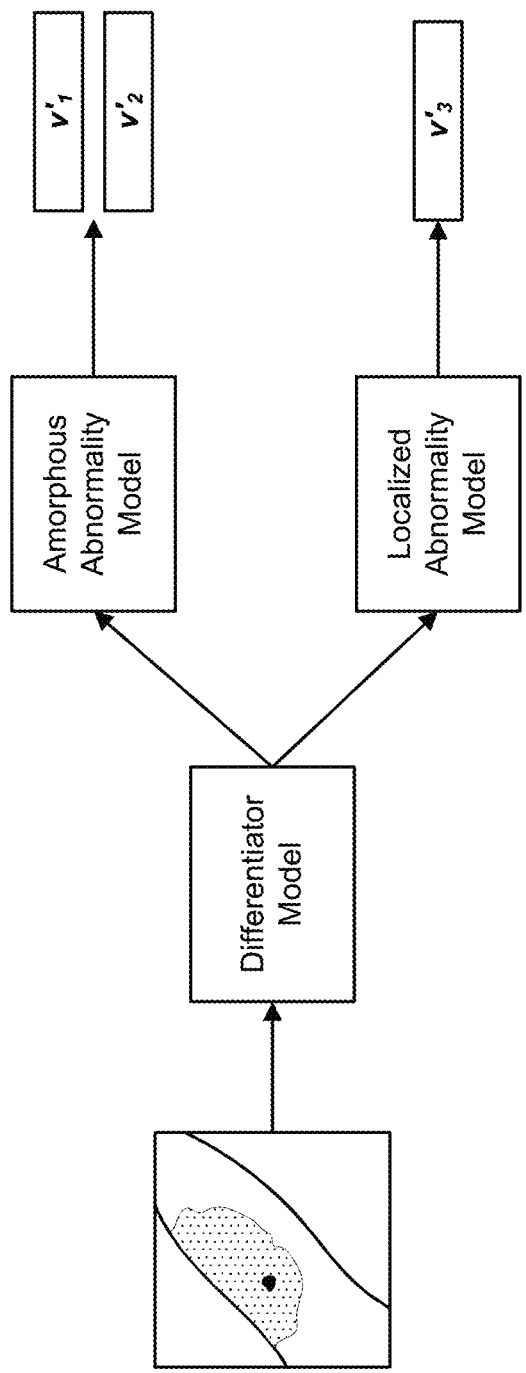
FIG. 6 illustrates an example inference process for a set of diagnosis models including a differentiator model for amorphous and localized skin abnormalities, in accordance with an embodiment.

FIG. 6 illustrates an example inference process for a set of diagnosis models including a differentiator model for amorphous and localized skin abnormalities, in accordance with an embodiment. In one embodiment, the set of machine-learned diagnosis models includes a differentiator model, an amorphous abnormality model, and a localized abnormality model. The differentiator model is configured to receive an input image and generate an indication on whether the input image includes an amorphous skin abnormality or a localized skin abnormality by applying a first set of trained weights. The amorphous abnormality model is configured to receive the input image and generate predictions on whether the input image includes one or more amorphous skin abnormalities, such as rashes, eczema by applying a second set of trained weights. The localized abnormality model is configured to receive the input image and generate predictions on whether the input image includes one or more localized skin abnormalities, such as moles, acne by applying a third set of trained weights.

Specifically, while amorphous skin abnormalities, such as rash, eczema, dermatitis, may manifest on the skin without a definitive shape or form, localized skin abnormalities, such as moles, may be more clearly defined to a local spot on the skin. Thus, due to the differences in shape and form, the diagnosis system 130 may obtain more accurate predictions by training two separate models where one model generates predictions for amorphous skin abnormalities, and another model that generates predictions for localized skin abnormalities.

During the inference process, the diagnosis system 130 generates an indication on whether the input image includes a localized or amorphous skin abnormality by applying the differentiator model to the input image. Rather than generate predictions that can be used to diagnose specific types of skin abnormalities (e.g., mole, acne, rash), the output of the differentiator model may simply indicate whether the input image includes any skin abnormality that can be classified as amorphous, and/or any skin abnormality that can be classified as localized. Responsive to determining that the input image includes amorphous skin abnormalities, the diagnosis system 130 generates specific predictions for one or more amorphous skin abnormalities by applying the amorphous abnormality model to the input image. Moreover, responsive to determining that the input image includes localized skin abnormalities, the diagnosis system 130 generates specific predictions for one or more localized skin abnormalities by applying the localized abnormality model to the input image.

Figure 7:
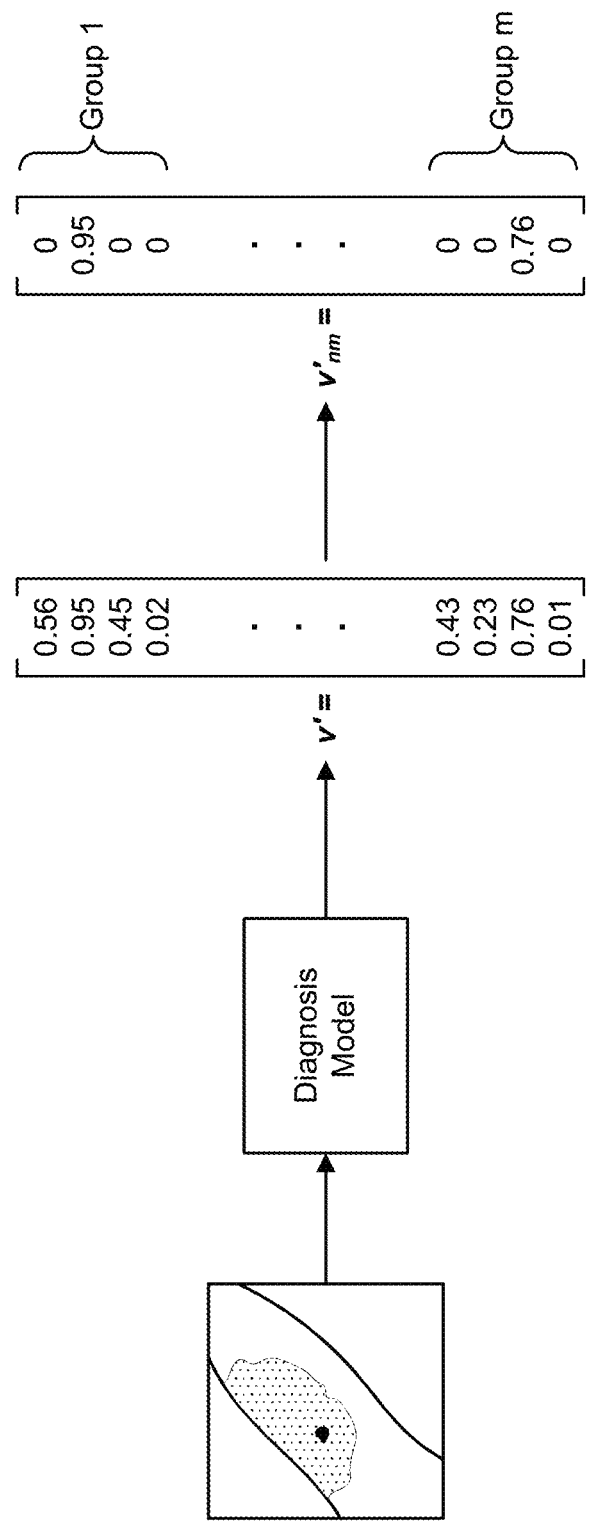
FIG. 7 illustrates an example inference process for a diagnosis model with non-maximal suppression, in accordance with an embodiment.

FIG. 7 illustrates an example inference process for a diagnosis model with non-maximal suppression, in accordance with an embodiment. In one embodiment, a machine-learned diagnosis model is configured to receive an input image and generate a vector that includes predictions for a list of health conditions. In the example shown in FIG. 7, the prediction v' generated by the diagnosis model may include one or more elements that each correspond to a prediction for a respective health condition. For example, the first element may correspond to a prediction that the input image includes eczema, the second element may correspond to a prediction that the input image includes dermatitis, and so on.

During the inference process, the diagnosis system 130 generates respective predictions for the two or more health conditions by applying the diagnosis model to the input image. In one embodiment, the diagnosis system 130 determines the diagnoses by using a non-maximal suppression. Specifically, the diagnosis system 130 splits the different health conditions represented by the vector v' into groups and for each group, selects only the health condition with the highest likelihood as part of the diagnoses. In one instance, the health conditions are grouped according to how similar their symptoms are visually presented on a patient, and thus, each group contains health conditions that diagnosis models are likely confused by in an image. In the example shown in FIG. 7, the health conditions for the first to fourth elements in the vector are assigned to "Group 1," and the health conditions for the n–3-th to n-th elements are assigned to "Group m." The diagnosis system 130 determines the diagnoses $v'_{nm}$ by selecting the health condition for the second element in "Group 1" and the n–1-th element in "Group m" and setting the remaining elements to zero, since each element has the highest likelihood in each group.

Returning to the system diagram of FIG. 1, the diagnosis system 130 may also train a set of machine-learned indicator models that are configured to receive an image of a patient and generate an indication on whether the input image presents two or more health conditions. Rather than actively diagnosing the specific health conditions themselves, the diagnosis system 130 may generate an indication on whether the input image presents two or more health conditions and provide the result to the user of the client device 110. Specifically, rather than generate predictions that can be used to diagnose specific types of health conditions, the output of the indicator model may simply determine whether the input image shows symptoms (e.g., overlapping symptoms) from two or more health conditions. Since input images presenting multiple health conditions may be difficult to diagnose, the user of the client device 110 can receive such an indication, in addition to or alternatively to an active diagnoses. The user can then determine to provide the input image to a medical expert to obtain a more accurate diagnoses.

Figure 8:
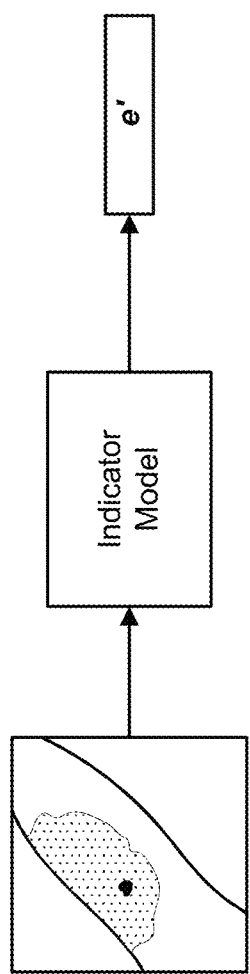
FIG. 8 illustrates an example inference process for an uncertainty model, in accordance with an embodiment.

FIG. 8 illustrates an example inference process for an indicator model, in accordance with an embodiment. In one embodiment, the diagnosis model trains a machine-learned indicator model configured to receive an input image and generate an indication e' on whether the input image presents two or more health conditions by applying a set of trained weights. In the example shown in FIG. 8, the diagnosis system 130 generates the indication e' by applying the indicator model to the input image. The diagnosis system 130 may simply provide the user of the client device 110 with information that the image includes too many health conditions for an accurate diagnoses.

In another embodiment, rather than training a separate indicator model as described in conjunction with FIG. 8, the diagnosis system 130 further incorporates the indicator function into a diagnosis model. For example, the diagnosis model may be configured to receive the input image and generate predictions on one or more health conditions included in the image and an indication whether the input image presents two or more health conditions. For example, the set of diagnosis models described in conjunction with FIGS. 2 through 7 may be further configured to generate such an indication in addition to the predictions for health conditions. As another example, the diagnosis model may be configured to generate a single output at a time, and may generate such an indication as the single output responsive to receiving an input image showing two or more health conditions.

In one instance, the diagnosis model is configured to generate such an indication by categorizing input images that present two or more health conditions as a separate category, and generating a likelihood for the separate category responsive to receiving the input image. In another instance, the diagnosis model is configured to generate such an indication when the predictions for the health conditions are output with relatively equal likelihoods or confidence levels, indicating ambiguity in the predictions. For example, the diagnosis system 130 may determine that an input image includes symptoms from two or more health conditions if the predictions for having a mole, a rash, a dermatosis are output to be 0.32, 0.29, 0.35, respectively.

In one embodiment, the diagnosis system 130 may determine that the input image presents two or more conditions if an indication likelihood is above a threshold likelihood, and that the input image presents a single health condition otherwise. In some embodiments, the indication may denote two likelihoods, a first likelihood on whether the input image presents two or more health conditions and a second likelihood on whether the input image presents a single health condition. The diagnosis system 130 may determine that the input image presents two or more conditions if the first likelihood is above a threshold and may determine that the input image presents a single health condition if the second likelihood is above a threshold.

Thus, in one embodiment, the diagnosis system 130 may receive a request for diagnoses of health conditions in an input image. The diagnosis system 130 may access an indicator model or a diagnosis model with indicator functionality from a database. The diagnosis system 130 can generate an indication representing a likelihood that the input image includes two or more health conditions by applying the indicator model to the input image. The diagnosis system 130 makes a determination on whether the input image presents two or more health conditions from the indication generated for the input image. The diagnosis system 130 generates a result for the request based on the determination and provides the result to the client device 110. The result can include a health care option for the individual in the input image based on the determination, and this suggested care option can be provided to the client device 110.

In one embodiment, the diagnosis system 130 may determine that the indication is unclear in that the diagnosis model 130 cannot make a definitive determination on whether the input image presents two or more health conditions. For example, this may occur when both the first likelihood (e.g., likelihood that image presents two or more health conditions) and the second likelihood (e.g., likelihood that image presents a single health condition) are both below a threshold (e.g., 80%). In such an embodiment, the diagnosis system 130 may output a result to the client device that the diagnoses cannot be made and can suggest, for example, that the user of the client device 110 obtain medical expertise.

In some embodiments, responsive to determining that the input image presents two or more skin abnormalities, the diagnosis system 130 may provide information about the indication to the client device 110 without providing predictions for the two or more health conditions in the input image. For example, the diagnosis system 130 may review and confirm governmental regulations and policies (e.g., regulations promulgated from the food and drug administration (FDA) or guidelines issued from the center for disease control (CDC), etc.), and generate results of the request to comply with these regulations. Thus, even if the diagnosis system 130 can generate predictions for two or more health conditions, the diagnosis system 130 may omit these results in the output to the client device 110 if the regulations place restrictions, for example, on the computerized diagnosis of two or more health conditions presented in an image. In such an embodiment, the diagnosis system 130 may simply provide the user with information that the input image contains two or more health conditions, but that a diagnoses cannot be made due to governmental regulations.

In some embodiments, responsive to determining that the input image presents a single health condition, the diagnosis system 130 may access and select a diagnosis model from the data base that is configured to generate a prediction for a single health condition. The diagnosis system 130 generates a prediction for the input image by applying the selected diagnosis model to the input image. The diagnosis system 130 generates a diagnosis for the single skin abnormality based on the prediction and provides the diagnosis as the result to the client device.

In some embodiments, responsive to determining that the input image presents two or more health conditions, the diagnosis system 130 may access and select a set of diagnosis models configured to generate a respective prediction for each of two or more health conditions from the database. For example, the diagnosis system 130 can access the models described in conjunction with FIGS. 2 through 7 that are configured to generate predictions for two or more health conditions. The diagnosis system 130 generates predictions for the two or more health condition in the input image by applying the set of diagnosis models to the input image. The diagnosis system 130 generates the diagnose for the input image from the predictions and provides the diagnoses as the result to the client device 110.

While the machine-learned models described in conjunction with FIGS. 2 through 8 are configured to receive input data in the form of images, the machine-learned models may also be configured to receive additional types of input data. For example, the additional types of input data may include biographical data of the patient such as height or weight of the patient, medical history of the patient, or patient answers to questions requesting information on existing medical conditions known to the patient, and the like. For example, the medical history of the patient may indicate that the patient is predisposed to certain health conditions that can affect the prediction outcome of the models.

Returning to the system diagram of FIG. 1, the client device 110 provides images of anatomical parts of a patient to the diagnosis system 130 such that the diagnosis system 130 can generate and display predictions or other indications on the client device 110. The user of the client device 110 can be a medical expert at a hospital that wishes to be assisted in the diagnosis of the patient's health conditions with computerized diagnostic systems. As another example, the user of the client device 110 can be an individual at home or in the office that wishes to obtain a diagnoses of underlying health conditions based on symptoms that are presented on the individual's body.

In one embodiment, the client device 110 includes a browser that allows the user of the client device 110 to interact with the diagnosis system 130 using standard Internet protocols. In another embodiment, the client device 110 includes a dedicated application specifically designed (e.g., by the organization responsible for the diagnosis system 130) to enable interactions among the client device 110 and the servers. In one embodiment, the client device 110 includes a user interface that allows the user of the client device 110 to interact with the diagnosis system 130 to view predictions of health conditions in the input image. For example, the user interface may be configured to overlay predictions generated by the diagnosis system 130 on locations on the image that are estimated to have the respective health conditions.

The client device 110 may be a computing device such as a smartphone with an operating system such as ANDROID® or APPLE® IOS®, a tablet computer, a laptop computer, a desktop computer, or any other type of network-enabled device that includes or can be configured to connect with a camera. In another embodiment, the client device 110 is a headset including a computing device or a smartphone camera for generating an augmented reality (AR) environment to the user, or a headset including a computing device for generating a virtual reality (VR) environment to the user. A typical client device 110 includes the hardware and software needed to connect to the network 122 (e.g., via WiFi and/or 4G or 5G or other wireless telecommunication standards).

The network 122 provides a communication infrastructure between the client devices 110 and the diagnosis system 130. The network 122 is typically the Internet, but may be any network, including but not limited to a Local Area Network (LAN), a Metropolitan Area Network (MAN), a Wide Area Network (WAN), a mobile wired or wireless network, a private network, or a virtual private network.

Architecture of Diagnosis System

Figure 9:
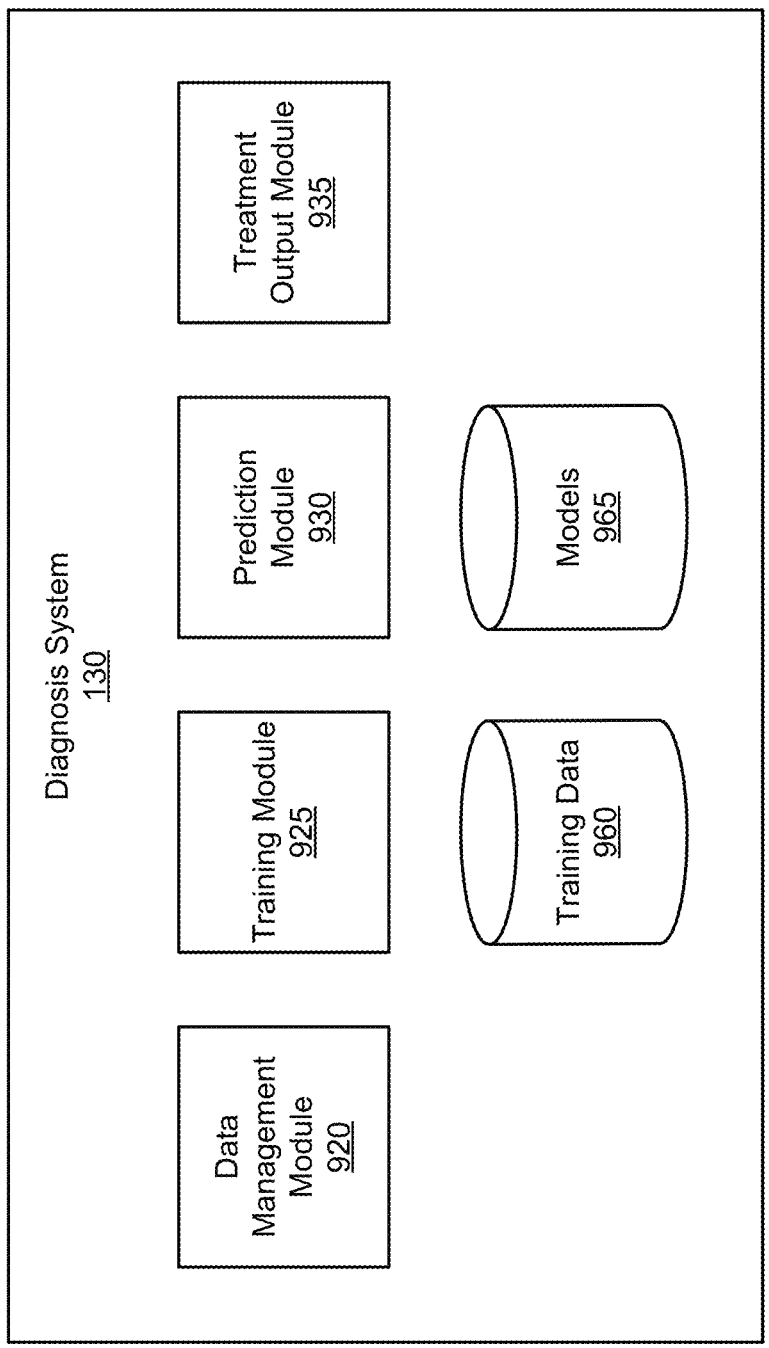
FIG. 9 is a block diagram of an architecture of a diagnosis system, in accordance with an embodiment.

FIG. 9 is a block diagram of an architecture of the diagnosis system 130, in accordance with an embodiment. The diagnosis system 130 shown by FIG. 9 includes a training module 920, a data management module 925, a training module 330, a prediction module 930, and a treatment output module 935. The diagnosis system 130 also includes a training datastore 960 and a models datastore 965. In alternative configurations, different and/or additional components may be included in the diagnosis system 130.

The data management module 920 obtains and manages training data stored in the training datastore 960 that can be used to train the set of models described in conjunction with the diagnosis system 130 in FIGS. 2 through 8. The training datastore 960 includes information extracted from images or videos of anatomical parts of individuals and known diagnoses of health conditions presented in these images. For example, the training datastore 960 may include information extracted from medical images, such as radiology images, computerized tomography (CT) scans, medical resonance imaging (MRI) scans, X-ray images, ultrasound or ultrasonography images, tactile images, or thermography images that are obtained by the data management module 920 from hospitals, medical image repositories, research image repositories, and the like. As another example, the training datastore 960 may include information extracted from images taken by individuals, such as images obtained on a smartphone camera that are obtained by the data management module 920 from users of client devices 110.

The training module 925 trains the set of models using information in the training datastore 960. Specifically, for a given diagnosis model $M_i$, the training data $S_i$ includes multiple training instances j=1, 2, . . . , $|S_i|$ each including input data $x_{j \in S}$ (e.g., training images or videos) and labels $y_{j \in S_i}$ that are known characterizations (e.g., diagnosis) of the input data $x_{j \in S}$. Specifically, the input data $x_j$ may include information extracted from a training image that captures an anatomical part of an individual. In one embodiment, when the machine-learned models are configured to receive additional types of data in addition to or alternatively to the input image, the input data $x_j$ s may also include the additional types of data (e.g., demographic information for the patient) for the patient in the training image. In one instance, the labels $y_{j \in S_i}$ may be obtained by human operators, such as medical doctors, medical experts, or other individuals that can verify the characterizations for the input data. In another instance, the labels themselves may be predictions generated by machine-learned models that are later validated by human operators.

The training module 925 trains the set of weights for a model by repeatedly iterating between a forward pass step and a backpropagation step. During the forward pass step, the training module 920 generates estimated outputs $y'_{j \in S}$ by applying the model with an estimated set of weights to the input data $x_j$ s across a corresponding subset $S_i$ of training data. The training module 920 determines a loss function that indicates a difference between the estimated outputs $y'_{j \in S}$ and the labels $y_{j \in S}$ for the plurality of training instances. During the backpropagation step, the training module 920 repeatedly updates the set of weights for the model by backpropagating error terms obtained from the loss function. The process is repeated until the change in loss function satisfies a predetermined criteria. For example, the criteria may be triggered if the change in loss function at each iteration is below a threshold.

In one embodiment, the loss function may be given by:

$$\mathcal{L}(y, y'_{j \in S}; \theta_p) = \sum_{j \in S} \|y_j - y'_j\|^2$$

for example, when the labels $y_j$ are continuous values, where $\theta_p$ are the set of weights for the diagnosis model. In another embodiment, the loss function may be given by:

$$\mathcal{L}(y_{j \in S}, y'_{j \in S}; \theta_p) = \sum_{j \in S} y_j \log y'_j + (1 - y_j) \log(1 - y'_j).$$

for example, when the labels $y_j$ are binary values. However, it is appreciated that the loss function can be any other function, such as an L1-norm, an L-infinity norm that indicates a difference between the actual labels and estimated outputs generated during each training interaction.

As described below, the training module 925 trains the set of diagnosis models described in conjunction with FIGS. 2 through 7 that can be used to determine active diagnoses of the input images. In one embodiment, one or more diagnosis models are configured to generate a prediction y'=v' as an output vector, where each element in the output vector v' corresponds to a prediction for a respective health condition. In such an embodiment, the training labels $y_j = v_j$ for the diagnosis model may be encoded as a one-hot encoded vector, where each element in the vector is a binary non-zero value (e.g., value of one) if the training image is diagnosed with the respective health condition for the element, and zero if there is no diagnosis. Thus, for training images presenting two or more health conditions, each respective element may be set to an appropriate value such that two or more elements in the vector have non-zero values. For example, the training data for a diagnosis model configured to predict a rash and a mole may include a label "[0 1]," where the first element indicates presence of a rash in the corresponding training image and the second element indicates absence of a mole in the training image. In another embodiment, a diagnosis model may be configured to generate a prediction y'=v' as an output value that can be assigned to one or more categories each representing a respective health condition. In such an embodiment, the label $y_j = v_j$ for the diagnosis model may be a value denoting the category for respective health condition diagnosed in the training image. For example, the training data for the example diagnosis model may include a label "1" indicating presence of a rash in the training image, or "2" indicating presence of a mole in the training image.

The training module 920 trains the set of weights for the ensemble set of diagnosis models described in conjunction with FIG. 3. Specifically, each diagnosis model in the ensemble set may be configured to generate predictions for a respective set of one or more health conditions. The diagnosis models in the ensemble set may differ from each other with respect to the architecture of the model, the set of health conditions that the models are configured to predict, and the like. In one embodiment, the diagnosis models are each configured as a neural network architecture that includes a set of layers of nodes, each layer connected to a previous layer via a set of weights. Thus, the diagnosis models in such an ensemble set may differ from each other with respect to the number of layers, nodes, and connections within the architecture.

The training module 925 trains the set of weights for a diagnostic model in the ensemble set using a training dataset that includes training images as input data $x_{j \in Si}$ and corresponding labels $y_{j \in S} = v_{j \in S}$ that indicate the presence of specific health conditions that the diagnosis model is configured to predict. During the forward pass step, the training module 925 generates estimated outputs $y'_{j \in S} = v'_{j \in S}$ by applying the diagnosis model to the training images. During the backpropagation step, the training module 925 repeatedly updates the set of weights for the diagnosis model with terms obtained from the loss function.

The training module 920 trains the set of weights for the feature extractor model and the feature classifier model described in conjunction with FIG. 4. In one embodiment, the feature extractor model and the feature classifier model are trained by training a neural network architecture including a first portion and a second portion. The set of weights for the first portion of the neural network architecture may be stored as the set of weights for the feature extractor model and the set of weights for the second portion may be stored as the set of weights for the feature classifier model. The set of weights for the feature classifier model are subsequently retrained using a plurality of components extracted from the training images.

Figure 10:
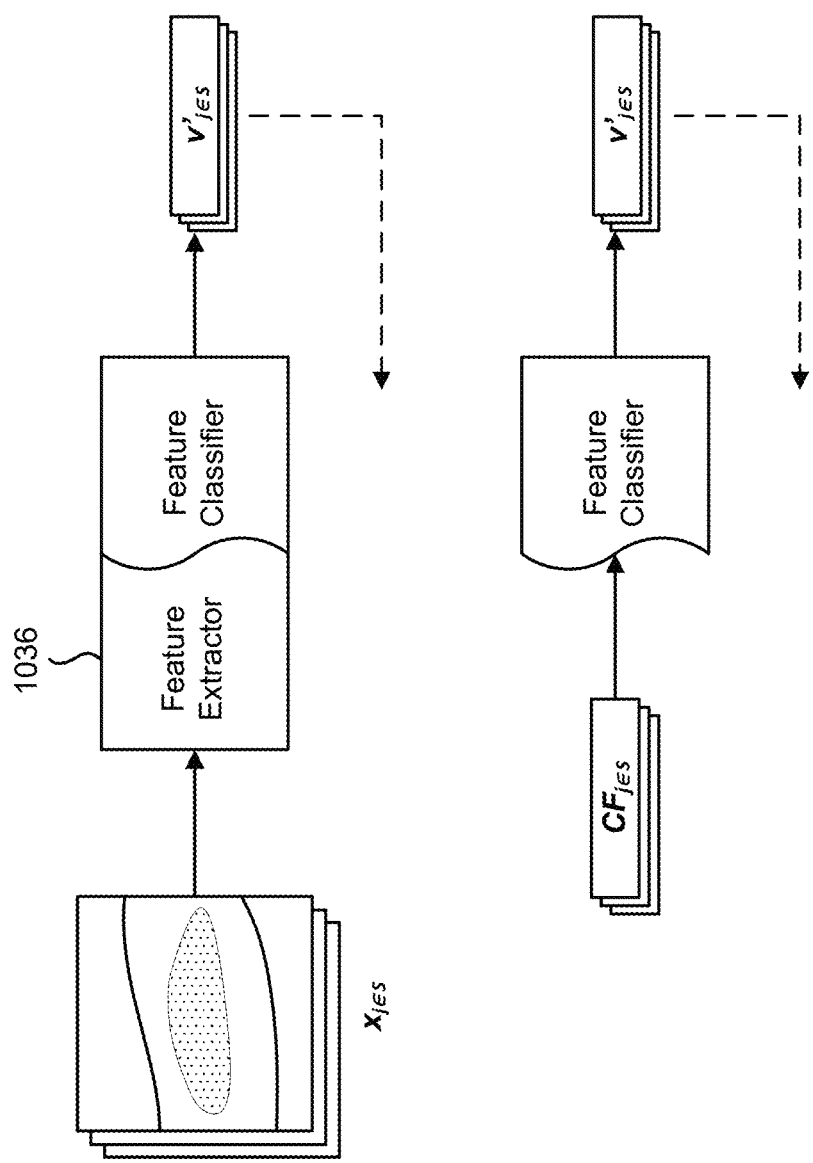
FIG. 10 illustrates an example training process for a set of diagnosis models shown in FIG. 4, in accordance with an embodiment.

FIG. 10 illustrates an example training process for a set of diagnosis models shown in FIG. 4, in accordance with an embodiment. The training module 925 trains a neural network architecture 1036 that includes a set of layers of nodes, each layer connected to a previous layer via a set of weights. The neural network architecture 1036 may be configured to generate predictions for a respective set of one or more health conditions. In one embodiment, the neural network architecture 1036 is configured as a deep neural network (DNN), a convolutional neural network (CNN), or any other types of neural network architectures that can receive image data and generate outputs.

The training module 925 trains the set of weights for the neural network architecture using a training dataset that includes training images as input data $x_{j \in S}$ and corresponding labels $y_{j \in S} = v_{j \in S}$ indicating the presence of specific health conditions that the feature classifier model is configured to predict. During the forward pass step, the training module 925 generates estimated outputs $y'_{j \in S} = v'_{j \in S}$ by applying the neural network architecture to the training images. During the backpropagation step, the training module 925 repeatedly updates the set of weights for the neural network architecture with terms obtained from the loss function.

After the training process for the neural network architecture has been completed, the training module 925 stores a first portion of the neural network architecture as the set of weights for the feature extractor model and a second portion of the neural network architecture as the set of weights for the feature classifier model. In one embodiment, the first portion and the second portion are selected such that the second portion includes the set of weights for layers placed after the layers for the first portion of the neural network architecture. For example, the first portion may include the set of weights for the first three layers of the neural network architecture, while the second portion may include the set of weights for the last five layers of the neural network architecture.

The training module 925 subsequently re-trains the set of weights for the feature classifier model using a training dataset that includes a plurality of components $CF_{j \in S}$ extracted from training images as input data $x_{j \in Si}$ and corresponding labels $y_{j \in S} = v_{j \in S}$ indicating the presence of specific health conditions in the training images that the feature classifier model is configured to predict. In one instance, the plurality of components for a training image is extracted by applying the trained feature extractor model to the training image to generate the image tensor for the training image, and performing ICA on the image tensor to generate the plurality of components. During the forward pass step, the training module 925 generates estimated outputs $y'_{j \in S} = v'_{j \in S}$ by applying the feature classifier model to the plurality of components $CF_{j \in S}$. During the backpropagation step, the training module 925 repeatedly updates the set of weights for the feature classifier model with terms obtained from the loss function.

The training module 925 trains the set of weights for the RNN architecture described in conjunction with FIG. 5. The training module 925 trains the set of weights for the RNN architecture using a training dataset that includes a sequence of training images as input data $x_{j \in S}$ and corresponding labels $y_{j \in S} = v_{j \in S}$ that indicate the presence of specific health conditions that the RNN architecture is configured to predict. In one embodiment, when the training data for the RNN architecture includes a sequence of training images presenting two or more health conditions, the label $v_j$ at each iteration of the sequence may be a one-hot encoded vector having a non-zero value at a respective one of the health conditions present in the training images. During the forward pass step, the training module 925 generates a sequence of estimated outputs $y'_{j \in S} = v_{j \in S}$ by repeatedly applying the RNN architecture to sequences of training images. In one embodiment, the labels $v_j$ may be re-ordered during the forward pass step of the training process, such that a difference, e.g., $|v_{j \in S} - v'_{j \in S}|$, is reduced or minimized over all or a subset of possible orderings. The training module 925 determines the loss function by combining the difference between the estimated output and the label at each iteration of the sequence. During the backpropagation step, the training module 925 repeatedly updates the set of weights for the RNN architecture with terms obtained from the loss function.

The training module 925 trains the differentiator model, the amorphous abnormality model, and the localized abnormality model described in conjunction with FIG. 6. The training module 925 trains the set of weights for the differentiator model using a training dataset that includes training images as input data $x_{j \in S}$ and corresponding labels $y_{j \in S} = s_{j \in S}$ indicating the presence of amorphous skin abnormalities or the presence of localized skin abnormalities. In one instance, the differentiator model is configured to generate the indication as a vector, where a first element corresponds to a likelihood that the image includes amorphous skin abnormalities and a second element corresponds to a likelihood that the image includes localized skin abnormalities. In such an instance, the labels $y_{j \in S}$ may be encoded such that the first element of the vector is a non-zero value (e.g., value of one) if the training image includes amorphous skin abnormalities, or zero if the image does not. Similarly, the second element of the vector is a non-zero value (e.g., value of one) if the training image includes localized skin abnormalities, or zero if the image does not. During the forward pass step, the training module 925 generates estimated outputs $y'_{j \in S} = s'_{j \in S}$ by applying the differentiator model to the training images, and repeatedly updates the set of weights for the differentiator model during the backpropagation step with terms obtained from the loss function.

The training module 925 trains the set of weights for the amorphous abnormality model using a training dataset that includes training images as input data $x_{j \in Si}$ and corresponding labels $y_{j\in S}=v_{j\in S}$ indicating the presence of specific amorphous skin abnormalities that the model is configured to predict. The training data for the amorphous abnormality model may include training images with a single amorphous skin abnormality or a plurality of amorphous skin abnormalities. During the forward pass step, the training module 925 generates estimated outputs $y'_{j\in S}=v'_{j\in S}$ by applying the amorphous abnormality model to the training images. During the backpropagation step, the training module 925 repeatedly updates the set of weights for the amorphous abnormality model with terms obtained from the loss function.

The training module 925 trains the set of weights for the localized abnormality model using a training dataset that contains training images as input data $x_{j\in S}$ and corresponding labels $y_{j\in S}=v_{j\in S}$ indicating the presence of specific localized skin abnormalities that the model is configured to predict. The training data for the localized abnormality model may include training images with a single localized skin abnormality or a plurality of localized skin abnormalities. During the forward pass step, the training module 925 generates estimated outputs $y'_{j\in S}=v'_{j\in S}$ by applying the localized abnormality model to the training images. During the backpropagation step, the training module 925 repeatedly updates the set of weights for the localized abnormality model with terms obtained from the loss function.

As further described below, the training module 925 further trains an indicator model described in conjunction with FIG. 8 that provides an indication of whether an image presents two or more health conditions. The training module 925 trains the set of weights for the indicator model using a training dataset that contains training images as input data $x_{j\in S}$ and corresponding labels $y_{j\in S}=e_{j\in S}$ indicating whether the training image presents two or more health conditions. The training data may include training images with symptoms from a single health condition or a plurality of health conditions. In one instance, the indicator model is configured to generate an indication representing a likelihood that an image presents two or more health conditions. In such an instance, the labels $y_{j\in Si}$ may be encoded as a non-zero value if the training image presents two or more health conditions, or zero if the training image presents a single health condition. During the forward pass step, the training module 925 generates estimated outputs $y'_{j\in S}=e'_{j\in S}$ by applying the indicator model to the training images. During the backpropagation step, the training module 925 repeatedly updates the set of weights for the indicator model with terms obtained from the loss function.

The training module 925 can also train a diagnosis model incorporated with the indicator functionality. The diagnosis model may be any model configured to generate computerized predictions on one or more health conditions in an image, such as the set of diagnosis models in FIG. 2 through 7, or diagnosis models configured to predict a single health condition. While the diagnosis model can generally be trained using diagnostic training data (e.g., training images and corresponding health condition labels), the training module 925 further trains the diagnosis model to incorporate the indicator functionality by including indicational training data for the diagnosis model in addition to the diagnostic training data.

In one embodiment, the indicational training data $S_a$ includes training images presenting two or more health conditions and corresponding labels $y_{j\in Sa}=v_{j\in Sa}$ that indicate the presence of the two or more health conditions in the training images. In one instance, when the labels $y_{j\in S}=v_{j\in S}$ for the diagnostic training data are one-hot encoded vectors, the labels $y_{j\in S}=v_{j\in Sa}$ for the indicational training data may be a vector having non-zero values for all or most elements in the vector. For example, the training data for a diagnosis model configured to predict a single health condition may include a label "[1 1]" that include non-zero values for all elements if a training image presents two or more health conditions. In this manner, the diagnosis model is configured to generate an indication by predicting relatively similar or equal likelihoods for all or most health conditions.

In another instance, the labels $y_{j\in Sa}=v_{j\in Sa}$ for the indicational training data may include an additional element or category to assign images presenting two or more health conditions. For example, when the labels $y_{j\in S}=v_{j\in S}$ for the diagnostic training data are one-hot encoded vectors, the labels may be further configured to include a separate element for the indication in addition to the elements for different health conditions. The separate element is a non-zero value if the training image presents two or more health conditions and zero if the training image does not. For example, the training data for a diagnosis model configured to predict a rash and/or a mole may include a label "[1 1 1]," where the first element indicates presence of a rash in the corresponding training image, the second element indicates presence of a mole in the training image, and the third separate element indicates the presence of two or more health conditions in the training image. As another example, when the labels $y_{j\in S}=v_{j\in S}$ for the diagnostic the labels are categories, the labels may be further configured to include a separate category for the indication in addition to the categories for different health conditions. For example, the training data for the example diagnosis model may include a label "1" indicating presence of a rash in the training image, "2" indicating presence of a mole in the training image, and "3" indicating presence of two or more health conditions in the training image.

The training module 925 may store the trained machine-learned models in the models datastore 965 such that they can be deployed during the inference process, in a manner described in conjunction with FIGS. 2 through 8.

The prediction module 930 receives requests from client devices 110 to provide computerized diagnoses of health conditions captured in an input image. Responsive to a request for diagnoses, the prediction module 930 may select a set of diagnosis models that can be used to generate diagnoses for an input image using the diagnosis models trained by the diagnosis system 130. The prediction module 930 may apply a selected diagnosis model to generate predictions on the health conditions presented in the input image, similarly to the example inference processes described in conjunction with FIGS. 2 through 8). In one instance, the prediction module 930 determines diagnoses for a health condition if the likelihood of the prediction is above a threshold. For example, the prediction module 930 may conclude that a respective health condition is definitely present in an input image if the prediction likelihood is above 0.80 or 80%. The prediction module 930 may conclude that a respective health condition is absent in the input image otherwise.

In some embodiments, the prediction module 930 determines that a prediction for a respective health condition is inconclusive, and may generate information that the diagnosis request cannot be made to the client device 110, or alternatively, may output the diagnoses for remaining health conditions that have definitive predictions to the client device 110. For example, the prediction module 930 may determine that a diagnosis is inconclusive if a respective prediction has a likelihood between the first and second thresholds (e.g., 20%-80%). In another instance, the prediction module 930 determines diagnoses for a health condition if the likelihood of the prediction is within a threshold proportion among other prediction likelihoods generated by the diagnosis model.

In one embodiment, the prediction module 930 is programmed to comply with relevant governmental regulations or policies governing computerized diagnostics, and generates diagnoses results to comply with current regulations and policies. For example, the regulations and policies may dictate various prediction thresholds that are used to determine whether a respective health condition is presented in an input image, and these thresholds may vary between different health conditions. In one instance, an administrator of the diagnosis system 130 may review these regulations and policies, and program the prediction module 930 to comply with them. In another instance, the prediction module 930 may collect information from the website or database of a relevant organization (e.g., FDA), and generate predictions according to the rules parsed from the collected information. Thus, the prediction module 930 may review the predictions generated by the models and generate diagnoses results for the request to comply with these regulations and policies. For example, the prediction module 930 may determine a diagnosis for acne if the prediction likelihood is over a threshold of 80%, while the prediction module 930 may determine a diagnosis for a rash if the prediction likelihood is only over a threshold of 95% according to policies set by the FDA.

Moreover, responsive to a request for a diagnoses, the prediction module 930 may select an indicator model or a diagnosis model with the indicator functionality to generate the indication for the input image. The prediction module 930 may apply the selected model to generate the indication. In one instance, the prediction module 930 determines that the input image presents two or more health conditions if the likelihood of the indication is above a threshold. In another instance, the prediction module 930 determines that the input image presents two or more health conditions if the likelihood of the indication is within a threshold proportion among other outputs generated by the selected model. As described in conjunction with FIG. 8, the prediction module 930 may generate a result for the request based on the determination such that appropriate diagnosis models can be selected to generate diagnoses, or information that the diagnoses cannot be made is output to the user of the client device 110, due to, for example, compliance with governmental regulations and policies on computerized diagnoses.

The treatment output module 935 provides potential treatment options in conjunction with the diagnoses provided by the prediction module 930. Given diagnoses results, it may be advantageous for the user of the client device 110 to receive potential options for treatment with the diagnoses such that they can, for example, treat the health condition within a short period of time if needed. In one embodiment, the treatment output module 935 may generate treatment options by consulting a human medical expert, reasoning of an expert system, or deriving the options from previous systems. In one embodiment, the treatment output module 935 may suggest treatment options that are known to reduce and avoid side-effects with respect to the health condition presented by the patient.

Method of Diagnosing Overlapping Skin Abnormalities

Figure 11:
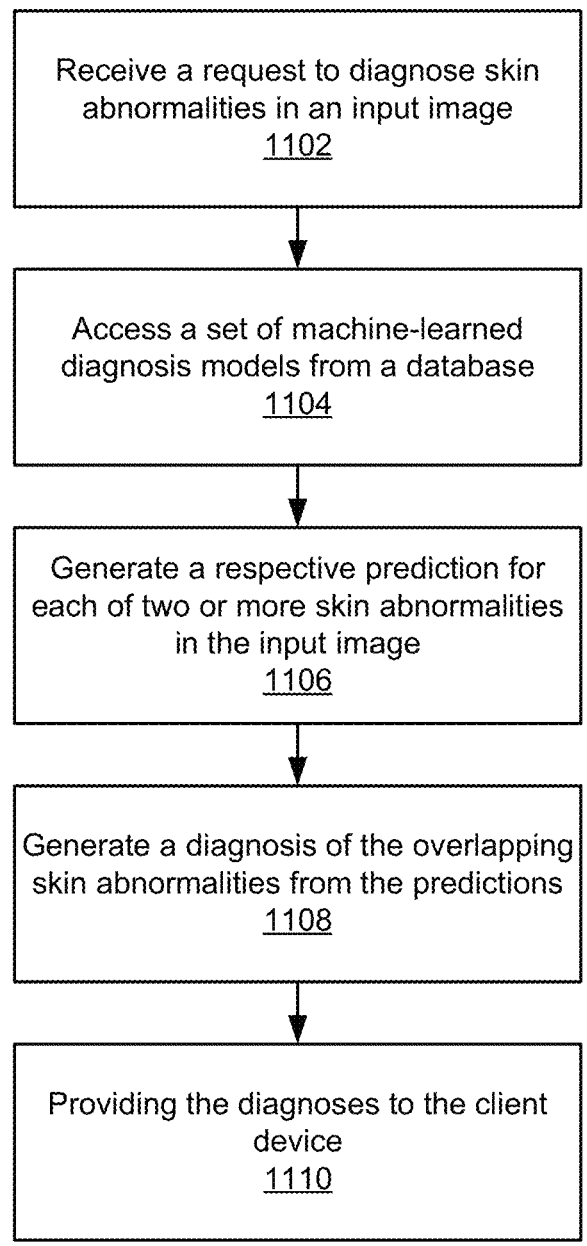
FIG. 11 illustrates an exemplary data flow for diagnosing overlapping skin abnormalities in an image, in accordance with an embodiment.

FIG. 11 illustrates a method of diagnosing overlapping skin abnormalities in an input image. The diagnosis system 130 receives 1102 (e.g., over network 120), from a client device, a request to diagnose skin abnormalities in an input image. The input image includes overlapping skin abnormalities on the skin of a patient. The diagnosis system 130 accesses 1104 (e.g., over network 120 using the prediction module 930) a set of machine-learned models from a database (e.g., models datastore 965, where the models 965 are trained using training data 960 and can include models described in conjunction with FIGS. 2 through 8). Each machine-learned model includes a respective set of trained weights. The diagnosis model 130 generates 1106 (e.g., using the prediction module 930) a respective prediction for each of two or more skin abnormalities in the input image by applying the set of machine-learned models to the input image (e.g., inference processes described in conjunction with FIGS. 2 through 8). A prediction indicates a likelihood that a respective skin abnormality in the two or more skin abnormalities are shown in the input image. The diagnosis system 130 generates 1108 (e.g., using the prediction module 930) a diagnosis of the overlapping skin abnormalities from the predictions. The diagnosis system 130 provides 1110 (e.g., over network 120) the diagnoses to the client device.

Method of Generating an Indication of Two or More Skin Abnormalities

Figure 12:
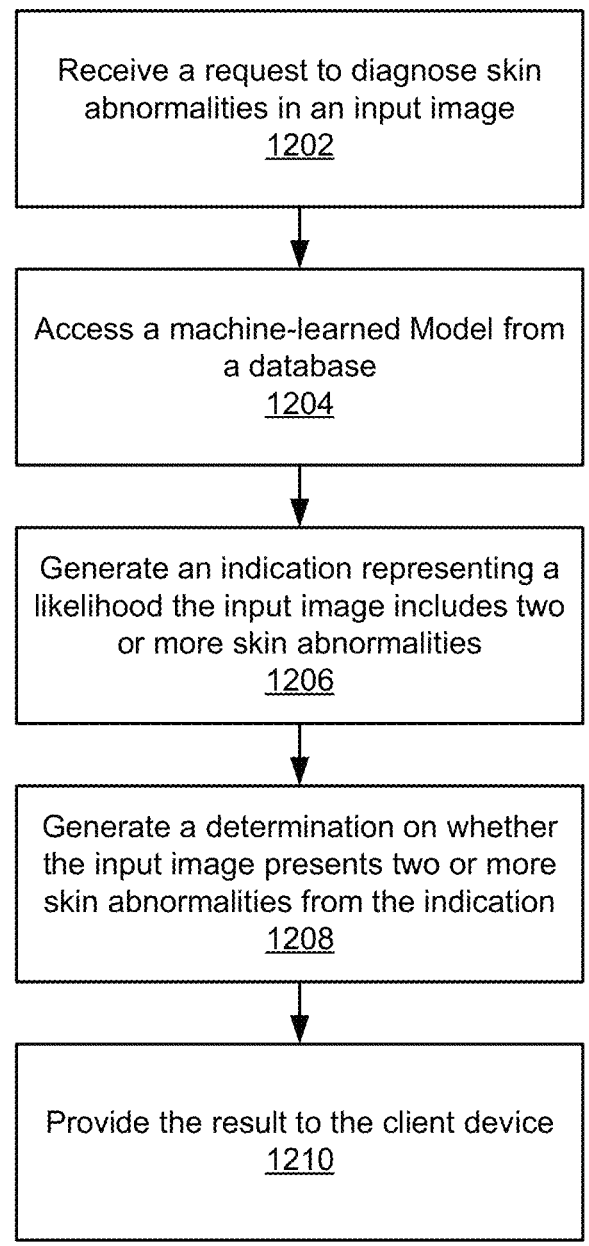
FIG. 12 illustrates an exemplary data flow of generating an indication of two or more skin abnormalities in an input image, in accordance with an embodiment.

FIG. 12 illustrates a method of generating an indication of two or more skin abnormalities in an input image. The diagnosis system 130 receives 1202 (e.g., over network 120), from a client device, a request for diagnoses of skin abnormalities in an input image. The diagnosis system 130 accesses 1204 (e.g., over network 120 using the prediction module 930) a machine-learned model from a database (e.g., models datastore 965, where the models 965 are trained using training data 960 and can include models described in conjunction with FIG. 8). The machine-learned model includes a respective set of trained weights. The diagnosis model 130 generates 1206 (e.g., using the prediction module 930) an indication by applying the machine-learned model to the input image (e.g., inference processes described in conjunction with FIG. 8). The diagnosis system 130 generates 1208 (e.g., using the prediction module 930) a result for the request based on the determination of the overlapping skin abnormalities from the predictions. The diagnosis system 130 provides 1210 (e.g., over network 120) the result to the client device.

SUMMARY

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method of generating an indication of two or more skin abnormalities in an input image, the method comprising:
    receiving, from a client device, a request for diagnoses of skin abnormalities presented in an input image;
    accessing a machine-learned model from a database, the machine-learned model including a respective set of trained weights, wherein the respective set of trained weights are trained using a respective training dataset including at least a training image and a label indicating whether the training image presents two or more skin abnormalities;
    generating an indication by applying the machine-learned model to the input image, the indication representing a likelihood that the input image shows two or more skin abnormalities;
    generating a determination on whether the input image presents two or more skin abnormalities from the indication generated for the input image; and
    generating a result for the request based on the determination, and providing the result to the client device.

2. The method of claim 1, further comprising determining a care option for the input image based on the determination, and providing the care option as the result to the client device.

3. The method of claim 1, further comprising:
    responsive to determining that the input image presents one skin abnormality, rather than two or more skin abnormalities, accessing a diagnosis model configured to generate a prediction for a single skin abnormality from the database;
    generating a prediction for the skin abnormality in the input image by applying the diagnosis model to the input image; and
    generating a diagnosis for the input image from the prediction, and providing the diagnosis as the result to the client device.

4. The method of claim 1, further comprising:
    responsive to determining that the input image presents two or more skin abnormalities, accessing a set of diagnosis models configured to generate a respective prediction for each of two or more skin abnormalities from the database;
    generating predictions for the two or more skin abnormalities in the input image by applying the set of diagnosis models to the input image; and
    generating diagnoses for the input image from the predictions, and providing the diagnoses as the result to the client device.

5. The method of claim 1, further comprising responsive to determining that the input image presents two or more skin abnormalities, providing information that the input image cannot be diagnosed to the client device.

6. The method of claim 1, further comprising responsive to the determining that the input image presents two or more skin abnormalities, providing information about the indication to the client device without providing predictions for the two or more skin abnormalities in the input image.

7. The method of claim 1, wherein the machine-learned model is also a diagnosis model further configured to receive an image and generate predictions for one or more skin abnormalities presented in the image.

8. The method of claim 7,
    wherein generating the indication further comprises applying the diagnosis model to the input image to generate an output vector including a set of elements, the predictions for the one or more skin abnormalities represented by values for the elements in the output vector, and
    wherein the input image is determined to present two or more skin abnormalities when differences between values of the set of elements in the output vector are below a predetermined threshold.

9. The method of claim 7, wherein generating the indication further comprises applying the diagnosis model to the input image to generate an output vector including a set of elements, wherein the predictions for the one or more skin abnormalities are represented by values for a subset of elements in the output vector, and wherein the indication is represented by a value of a remaining element in the output vector.

10. The method of claim 7,
    wherein the predictions for the one or more skin abnormalities are represented by one or more categories in a set of categories,
    wherein generating the indication further comprises applying the diagnosis model to the input image to generate an output value, and
    wherein the input image is determined to present two or more skin abnormalities when the output value is assigned to a remaining category in the set of categories.

11. The method of claim 1, wherein the respective training dataset includes at least a first training image and a first label indicating that the first training image presents a single skin abnormality, and a second training image and a second label indicating that the second training image presents two or more skin abnormalities.

12. The method of claim 1, wherein the respective set of weights are trained by:
applying weights of the machine-learned model to the training image to generate an estimated output;
computing a loss function indicating a difference between the estimated output and the label; and
backpropagating terms obtained from the loss function to update the weights of the machine-learned model.

13. A non-transitory computer program product for generating an indication of two or more skin abnormalities in an input image, the computer program product comprising a computer-readable storage medium containing computer program code for:
receiving, from a client device, a request for diagnoses of skin abnormalities in an input image;
accessing a machine-learned model from a database, the machine-learned model including a respective set of trained weights, wherein the respective set of trained weights are trained using a respective training dataset including at least a training image and a label indicating whether the training image presents two or more skin abnormalities;
generating an indication by applying the machine-learned model to the input image, the indication representing a likelihood that the input image includes two or more skin abnormalities;
generating a determination on whether the input image presents two or more skin abnormalities from the indication generated for the input image; and
generating a result for the request based on the determination, and providing the result to the client device.

14. The non-transitory computer program product of claim 13, wherein the computer-readable storage medium further contains computer program code for determining a care option for an individual in the input image based on the determination, and providing the care option as the result to the client device.

15. The non-transitory computer program product of claim 13, wherein the computer-readable storage medium further contains computer program code for:
responsive to determining that the input image presents one skin abnormality, rather than two or more skin abnormalities, accessing a diagnosis model configured to generate a prediction for a single skin abnormality from the database;
generating a prediction for the skin abnormality in the input image by applying the diagnosis model to the input image; and
generating a diagnosis for the input image from the prediction, and providing the diagnosis as the result to the client device.

16. The non-transitory computer program product of claim 13, wherein the computer-readable storage medium further contains computer program code for:
responsive to determining that the input image presents two or more skin abnormalities, accessing a set of diagnosis models configured to generate a respective prediction for each of two or more skin abnormalities from the database;
generating predictions for the two or more skin abnormalities in the input image by applying the set of diagnosis models to the input image; and
generating a diagnoses for the input image from the predictions, and providing the diagnoses as the result to the client device.

17. The non-transitory computer program product of claim 13, wherein the computer-readable storage medium further contains computer program code for responsive to determining that the input image presents two or more skin abnormalities, providing information that the input image cannot be diagnosed to the client device.

18. The non-transitory computer program product of claim 13, wherein the computer-readable storage medium further contains computer program code for responsive to the determining that the input image presents two or more skin abnormalities, providing information about the indication to the client device without providing predictions for the two or more skin abnormalities in the input image.

19. The non-transitory computer program product of claim 13, wherein the machine-learned model is also a diagnosis model further configured to receive an image and generate predictions for one or more skin abnormalities presented in the image.

20. The non-transitory computer program product of claim 19,
wherein generating the indication further comprises applying the diagnosis model to the input image to generate an output vector including a set of elements, the predictions for the one or more skin abnormalities represented by values for the elements in the output vector, and
wherein the input image is determined to present two or more skin abnormalities when differences between values of the set of elements in the output vector are below a predetermined threshold.

21. The non-transitory computer program product of claim 19, wherein generating the indication further comprises applying the diagnosis model to the input image to generate an output vector including a set of elements, wherein the predictions for the one or more skin abnormalities are represented by values for a subset of elements in the output vector, and wherein the indication is represented by a value of a remaining element in the output vector.

22. The non-transitory computer program product of claim 19,
wherein the predictions for the one or more skin abnormalities are represented by one or more categories in a set of categories,
wherein generating the indication further comprises applying the diagnosis model to the input image to generate an output value, and
wherein the input image is determined to present two or more skin abnormalities when the output value is assigned to a remaining category in the set of categories.

23. The non-transitory computer program product of claim 13, wherein the respective training dataset includes at least a first training image and a first label indicating that the first training image presents a single skin abnormality, and a second training image and a second label indicating that the second training image presents two or more skin abnormalities.

24. The non-transitory computer program product of claim 13, wherein the respective set of weights are trained by:

applying weights of the machine-learned model to the training image to generate an estimated output;
computing a loss function indicating a difference between the estimated output and the label; and
backpropagating terms obtained from the loss function to update the weights of the machine-learned model.

* * * * *